(12) United States Patent
Hunger et al.

(10) Patent No.: US 11,925,744 B2
(45) Date of Patent: Mar. 12, 2024

(54) MEDICAL FLUSHING PUMP COMPRISING TWO SUCTION LINES

(71) Applicant: W.O.M. WORLD OF MEDICINE GMBH, Berlin (DE)

(72) Inventors: Christian Hunger, Oranienburg (DE); Lucile Tartivel, Berlin (DE); Jan Hendrik Carstens, Berlin (DE); Mike Plessner, Friesack (DE); Nils Gelbert, Berlin (DE); Stan Schnuettgen, Berlin (DE); Oliver Rath, Berlin (DE); Thomas Christmann, Berlin (DE)

(73) Assignee: W.O.M. WORLD OF MEDICINE GMBH, Berlin (DE)

( * ) Notice: Subject to any disclaimer, the term of this patent is extended or adjusted under 35 U.S.C. 154(b) by 0 days.

(21) Appl. No.: 17/311,389

(22) PCT Filed: Dec. 4, 2019

(86) PCT No.: PCT/DE2019/000312
§ 371 (c)(1),
(2) Date: Jun. 7, 2021

(87) PCT Pub. No.: WO2020/114534
PCT Pub. Date: Jun. 11, 2020

(65) Prior Publication Data
US 2022/0023524 A1  Jan. 27, 2022

(30) Foreign Application Priority Data

Dec. 7, 2018 (DE) .................... 10 2018 009 537.2
Jul. 5, 2019 (DE) .................... 10 2019 004 629.3

(51) Int. Cl.
*A61M 1/00* (2006.01)

(52) U.S. Cl.
CPC .............. *A61M 1/743* (2021.05); *A61M 1/60* (2021.05); *A61M 1/77* (2021.05)

(58) Field of Classification Search
CPC .................................................. A61M 1/743
See application file for complete search history.

(56) References Cited

U.S. PATENT DOCUMENTS

| 6,871,660 | B2 * | 3/2005 | Hampsch | F16K 31/465 251/294 |
| 7,371,224 | B2 * | 5/2008 | Haischmann | A61B 17/320016 604/31 |
| 2003/0069549 | A1 * | 4/2003 | MacMahon | A61M 1/67 604/266 |
| 2012/0090620 | A1 | 4/2012 | Deutsch | |

(Continued)

FOREIGN PATENT DOCUMENTS

| EP | 0173816 A2 | 3/1986 | |
| EP | 624382 A1 * | 11/1994 | ......... A61M 39/281 |

(Continued)

*Primary Examiner* — Catharine L Anderson
*Assistant Examiner* — Arjuna P Chatrathi
(74) *Attorney, Agent, or Firm* — Stuart H. Mayer; Kaplan Breyer Schwarz LLP

(57) ABSTRACT

The present invention relates to a device for flushing a body cavity with a fluid, the fluid being pumped by means of two lines from the body cavity. The respective pumping capacity is regulated via controllable pinch valves, the two pinch valves being coupled in an antiparallel manner.

1 Claim, 3 Drawing Sheets

(56) References Cited

U.S. PATENT DOCUMENTS

Figure 1:
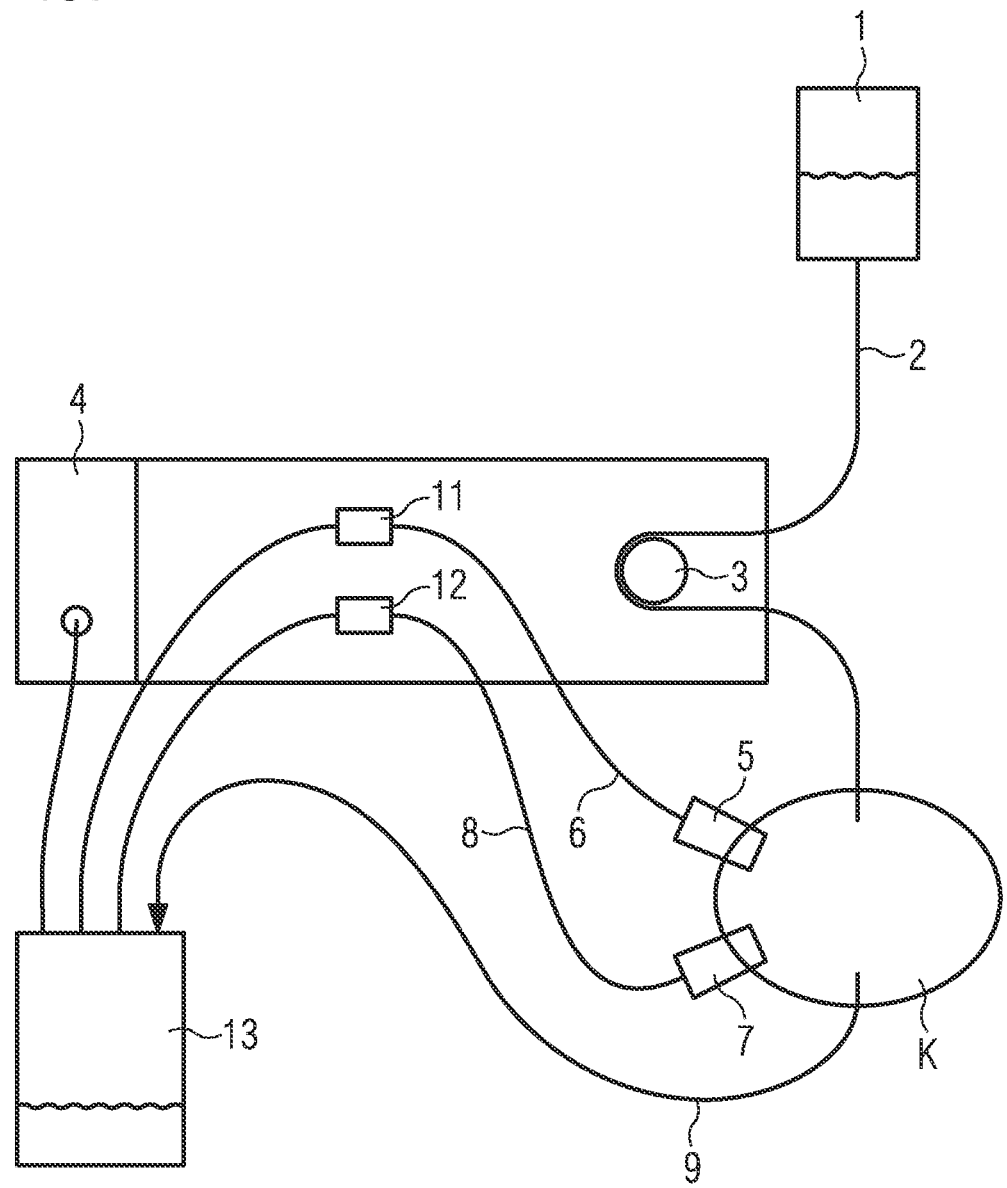

2013/0267779 A1* 10/2013 Woolford ............... A61B 17/34
                                                      600/156
2018/0245699 A1*  8/2018 Lee ........................ F16K 7/06

FOREIGN PATENT DOCUMENTS

EP           1374925 B1    4/2006
WO     WO-2006083244 A1 *  8/2006  .......... A61M 39/223

* cited by examiner

MEDICAL FLUSHING PUMP COMPRISING TWO SUCTION LINES

The present invention relates to a device for flushing a body cavity with a fluid, the fluid being pumped by means of two lines from the body cavity. The respective pumping capacity is regulated via controllable pinch valves, the two pinch valves being coupled in an antiparallel manner.

FIELD OF THE INVENTION

It is known, in endoscopic examinations and in particular in therapeutic interventions, to perform liquid flushings. Herein, the body cavity (e.g., a joint cavity, a bladder, or a uterus) is flushed with a liquid (e.g., saline solution). For this purpose, a flushing liquid from a storage container may be pumped via a pump, e.g., a roller wheel pump, into the body cavity. In the simplest case, the flushing liquid may run out again through an opening from the cavity. Normally, however, suction pumps are employed to pump the flushing liquid off again. In a typical course of such minimal-invasive interventions, the use of further medical devices each having an own suction line for cutting, ablating, or atrophying is provided. When all these suction lines are open, no pressure can be created to distend the body cavity. Typically, as few incisions in the walls of the body as possible should be made, and therefrom results that one supply line is combined with multiple suction lines.

In therapeutic interventions in body cavities (e.g., knee or shoulder joint or bladder or uterus or other artificial body cavities), often two medical instruments are used, namely a shaver and a high-frequency (HF) ablation device. Further, it has proven advantageous, when both medical instruments are connected to a suction line. A challenge, herein, is the control of the suction capacity. On the one hand, the sucked liquid volume has to correspond to the flowing-in volume, since otherwise either the necessary distention of the body cavity is not secured anymore or else the pressure in the body cavity will increase such that tissue injuries may occur. On the other hand, it is reasonable that pumping-off of the volume takes place in particular via the exit line of the respective instruments.

Further, it is state of the art to pinch the suction lines by so-called pinch valves having a solenoid coil or a linear solenoid by a stamp and thus to close them. This fulfills the condition that the medium used for distention does not contact the device, and the medium, thus, reaches the body cavity via a sterile tube. The force that the solenoid coil imposes on the tube, is, however, directly proportional to the speed, i.e., with a high switching frequency, a high load on the abutment of the tube and the tube material is caused.

The medical device described in the following guarantees in a simple way that the above objects can be solved: There is pumped off exactly as much volume from the body cavity, as is supplied thereto. Furthermore, pumping-off mainly occurs via the exit line of the respectively operated instrument.

Further, an improved pinch valve control was developed.

Figure 2A:
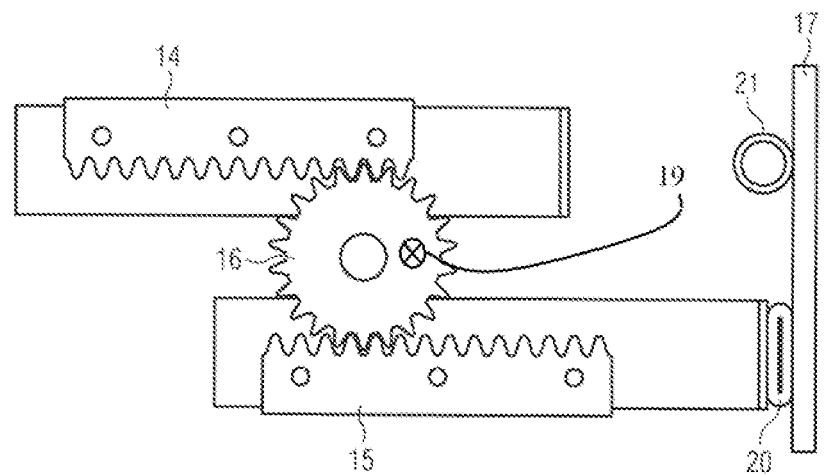
Figure 2B:
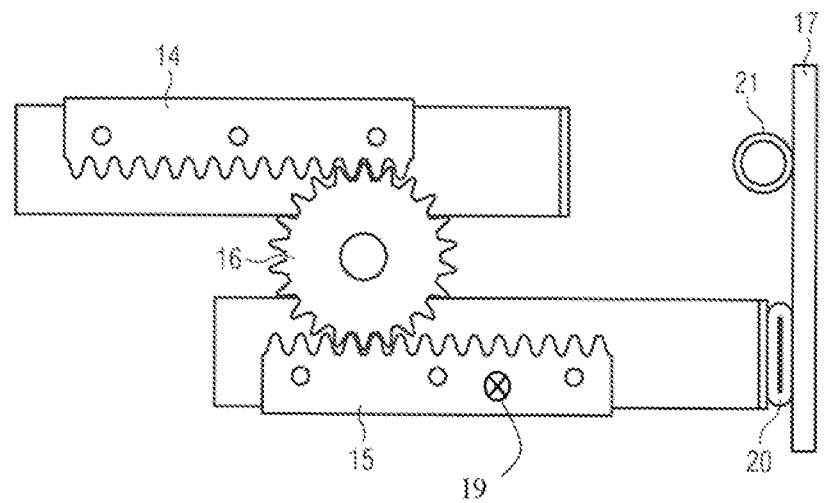

The device according to the invention is described in FIGS. 1, and 2A and 2B, to which reference is made hereby.

In the context of the device according to the invention, first, a storage container for the flushing liquid is installed. The supply line from this storage container leads over a controlled roller wheel pump into the body cavity. Coupling of the supply line to the roller wheel suitably occurs by a corresponding cartridge, as it is known in prior art. For suction from the body cavity serves a controlled vacuum pump. The two medical instruments (e.g., shaver and high-frequency-ablation device) each comprise a suction line. The two lines are each provided with a pinch valve, which is described below in more detail. The exit lines lead, in the direction of flow behind the pinch valves, into a storage container. This storage container is connected to the controlled vacuum pump. The storage container is installed such that the sucked-off liquid collects therein and does not reach the vacuum pump.

Normally, still another line is installed between the body cavity and the storage container. This additional line includes a throttle so that in any case very little flushing liquid only is sucked off (less than 10% of the total volume flow). Throttling of the volume flow may occur by a correspondingly reduced tube diameter. The additional line only serves for the generation of a constant flow, to discharge occurring smaller bleedings and tissue debris, and to thus enable a good view into the fluid-filled body cavity.

Important elements of the described medical device are the pinch valves. They are coupled to each other in such a manner that one line is completely open when the other line is completely closed. For this purpose serves a stepper motor that drives two gear racks via a gear wheel. The two gear racks are respectively positioned opposite to each other at the gear wheel so that one gear rack exits the device, when the other one enters (antiparallel operation). The two tubes are each positioned in a clamping device that at the same time serves as an abutment for the gear racks serving as a pinching device. By controlling the stepper motor, it can be selected through which line the flushing liquid is sucked off. In the respective end positions, suction occurs either completely via the one line or completely via the other line (volume flow ratio 100:0 or 0:100). There are also possible, however, intermediate positions, so that, for instance, the liquid flow is divided in a proportion of 80:20 or 60:40.

The pinch elements firmly connected to the gear racks act on the tube portions to be clamped and exert a pressure, as in prior art, that leads to deformation and even to closure of the tube lumen.

An optional feature of the invention is a position sensor provided at the gear wheel, which enables, at any point of time, an absolute determination of the position of the gear wheel. It is advantageous, herein, that even in a standstill situation, the position can be determined and no movement at the position sensor is required, the consequence of which would be a partial or short-term opening of the clamped tube lumen. This property is utilized for another feature of the invention, namely a drive control for the gear wheel being variable in the course of the closure phase, such that, in the switching phase, the gear racks can very quickly be moved, and in the clamping phase or part of the clamping phase until final closure, the movement occurs with a drive power that corresponds to a defined and predetermined pressure on the tube to be clamped. In order to achieve this, the drive device is configured, also according to the invention, such that a motor-gear combination to be used therefore is adapted such that with the minimally required force for clamping, the maximally possible speed in the switching phases is attainable.

According to the invention, a motor-gear combination is selected that can attain a maximally achievable pinching force. By coupling increasing force transfer and decreasing speed of travel in the gears, a speed of travel achievable with full speed of the motor is determined by the definition of the maximally achievable pinching force. This is on the condition that the used components are not oversized and thus as cost-effective as possible. The selection rule according to the invention is, therefore, to first dimension the motor-gear combination for moving the gear in such a way that the required pressure force can just be generated, in order to clamp the tubes and thus to securely close them. Thus, the maximally achieved speed of travel of the motor-gear combination will be higher than for motor-gear combinations that generate a stronger pressure force. The required pressure force can be determined by a measurement of the pressure on the tube to be clamped up to the closure thereof.

Optionally, the position sensor may also be attached at one of the gear racks. It is also possible to employ several position sensors (e.g., at gear rack and gear wheel or at both gear racks).

An advantage of the valve control according to the invention is that a design of the tube portions and the abutment may be performed in such a way that less robust and thus lower-cost material can be used or material can be saved and at the same time, a maximally quick closure of the suction lines can occur.

The valve control according to the invention is achieved in such a manner that the actual position of the gear racks determined by the position sensor affects the speed of travel. The speed of travel is maximum in the phases, in which there is no contact of the pinch elements or the gear racks with the tube to be pinched. The drive unit is designed for this maximum speed of travel. According to a speed profile of the invention, a reduction of the speed to 50% in the last 10 to 20% of the travel, i.e., until the tube is completely pinched, is performed. With this reduction of the pinching speed of the tube lumen, pressure pulses in the suction line are avoided, and the tube material and the abutment are protected, thus the lifetime of the tube and the cartridge or tube-insertion aid containing the tube is extended. This is not possible with linear solenoids. Different values for the speed of travel reduction and the points of time when the speed of travel is changed, including continuous changes and several stages, also fall under the invention.

A continuation of the spirit of the invention is a speed-of-travel profile, in which for a short travel before the tube contact, the speed of travel is reduced, and at the occasion of tube contact an increase of the speed of travel occurs, with a subsequent continuous reduction to zero in the position, where the tube is completely pinched. Other profiles with any combinations of increase and reduction of the speed of travel also fall under the invention.

At the beginning of the treatment, first, via the roller wheel pump, flushing liquid is pumped into the body cavity, until the required pressure or the required distention of the body cavity is achieved. When the required pressure is achieved, the suction pump is activated, with the powers of the roller wheel pump and the suction pump being coupled. It is pumped so much liquid only as is supplied. Upon the activation of the medical instruments (e.g., shaver and high-frequency-ablation device), the pinch valves are respectively adjusted such that the pumping capacity mainly leads over the exit line of the respective instrument. When the shaver is activated, the exit line connected to the shaver is opened, and the line connected to the high-frequency-ablation device is closed. When, at a later point in time, the other medical device is used, the other line is opened, and the first line is closed. As already described above, opening or closing may also occur partially. In this case, for instance, 80% of the suction capacity would occur through the suction line connected to the activated medical instrument, whereas 20% of the suction capacity would be conducted via the other instrument. At the end of the procedure, there is the possibility to stop the roller wheel pump, but to activate the suction pump until the flushing liquid has been sucked off as far as possible.

LIST OF REFERENCES (1) storage container for the flushing liquid,
(2) supply line,
(3) controlled roller wheel pump,
(4) controlled vacuum pump,
(5) first medical instrument,
(6) first suction line,
(7) second medical instrument,
(8) second suction line,
(9) third suction line (optional),
(10) throttle at optional third suction line,
(11) first pinch valve,
(12) second pinch valve,
(13) waste container,
(14) first gear rack with first pinch element,
(15) second gear rack with second pinch element,
(16) gear wheel,
(17) abutment for pinch element at first gear rack with inserted and clamped tube (20),
(18) abutment for pinch element at second gear rack with inserted and not clamped tube (21),
(19) position sensor.

The invention claimed is:

1. A device for flushing a body cavity (K), comprising
(i) a storage container (1) for the flushing liquid,
(ii) a supply line (2),
(iii) a controlled roller wheel pump (3),
(iv) a controlled vacuum pump (4),
(v) a first medical instrument (5) with a first suction line (6),
(vi) a second medical instrument (7) with a second suction line (8),
(vii) optionally a third suction line (9) with a throttle (10),
(viii) a first pinch valve (11) at the first suction line (6),
(ix) a second pinch valve (12) at the second suction line (8),
(x) a waste container (13), connected to the first suction line (6), second suction line (8), and optional third suction line (9), and to the controlled vacuum pump (4),
characterized by that the first pinch valve (11) and the second pinch valve (12) are coupled in an anti-parallel manner,
wherein the antiparallel coupling takes place such that the first and the second pinch valves (11, 12) are formed by pinch elements that are respectively attached on two gear racks (14, 15), and the two gear racks (14, 15) are coupled to each other by means of a gear wheel (16), so that they are moved for an antiparallel movement,
wherein one or more position sensors (19) provided at the gear wheel (16) and/or the two gear racks (14, 15), which enables, at any point of time, an absolute determination of a position of the gear wheel (16) and the two gear racks (14, 15) moved thereby,
wherein the gear wheel (16) is driven by a motor-gear combination which is selected such that a speed of travel of the two gear racks (14, 15) is maximum in the phases, in which there is no contact of the pinch elements or the two gear racks with a tube to be pinched and that a reduction of the speed of the two gear racks to 50% in the last 10 to 20% of the travel, until the tube is completely pinched, is performed, and wherein the motor-gear combination driving the gear wheel (16) which in turn move the two gear racks (14, 15) provides a speed-of-travel profile, in which for a short travel before the tube contact, the speed of travel is reduced, and at an occasion of tube contact of one of the two gear racks an increase of speed of travel occurs, with a subsequent continuous reduction to zero in the position, in which the tube is completely pinched.

\* \* \* \* \*